United States Patent [19]

Weitschies et al.

[11] Patent Number: 6,068,857
[45] Date of Patent: *May 30, 2000

[54] MICROPARTICLES CONTAINING ACTIVE INGREDIENTS, AGENTS CONTAINING THESE MICROPARTICLES, THEIR USE FOR ULTRASOUND-CONTROLLED RELEASE OF ACTIVE INGREDIENTS, AS WELL AS A PROCESS FOR THEIR PRODUCTION

[75] Inventors: Werner Weitschies; Dieter Heldmann; Peter Hauff; Thomas Fritzsch; Harald Stahl, all of Berlin, Germany

[73] Assignee: Schering Aktiengesellchaft, Berlin, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/605,174

[22] PCT Filed: Aug. 25, 1994

[86] PCT No.: PCT/EP94/02806

§ 371 Date: Aug. 5, 1996

§ 102(e) Date: Aug. 5, 1996

[87] PCT Pub. No.: WO95/07072

PCT Pub. Date: Mar. 16, 1995

[30] Foreign Application Priority Data

Sep. 9, 1993 [DE] Germany .............................. 43 30 958
May 11, 1994 [DE] Germany .............................. 44 16 818

[51] Int. Cl.[7] .............................. A61K 9/52; B01J 13/04; B01J 3/04

[52] U.S. Cl. .............................................. 424/489; 424/9.1

[58] Field of Search ................................ 424/489

[56] References Cited

U.S. PATENT DOCUMENTS

| 5,190,766 | 3/1993 | Isihara et al. ............................ 424/489 |
| 5,529,766 | 6/1996 | Klaueness et al. ..................... 424/9.52 |
| 5,562,893 | 10/1996 | Lohrmann ............................... 424/9.52 |
| 5,611,344 | 3/1997 | Bernstein et al. ................. 128/662.02 |

FOREIGN PATENT DOCUMENTS

| 0504881 | 9/1992 | European Pat. Off. . |
| 9222298 | 12/1992 | WIPO . |
| 9300933 | 1/1993 | WIPO . |

OTHER PUBLICATIONS

J. Cummings, *Exp. Opin. Ther. Patents* (1993) 8(2) pp. 153–171, "Microspheres as a Drug Delivery System in Cancer Therapy".

*Primary Examiner*—Peter F. Kulkosky
*Attorney, Agent, or Firm*—Millen, White, Zelano & Branigan, P.C.

[57] ABSTRACT

The invention relates to new microparticles containing active ingredients, which contain at least one gas or a gaseous phase in addition to the active ingredient(s), agents containing these particles (microparticulate systems), their use for ultrasound-controlled in vivo release of active ingredients, as well as a process for the production of particles and agents.

23 Claims, No Drawings

MICROPARTICLES CONTAINING ACTIVE INGREDIENTS, AGENTS CONTAINING THESE MICROPARTICLES, THEIR USE FOR ULTRASOUND-CONTROLLED RELEASE OF ACTIVE INGREDIENTS, AS WELL AS A PROCESS FOR THEIR PRODUCTION

The invention relates to the object characterized in the claims, i.e., new microparticles which contain active ingredients and contain at least one gas or a gaseous phase in addition to the active ingredient(s), agents containing these particles (microparticulate systems), their use for ultrasound-controlled in vivo release of active ingredients, for ultrasound-supported cell incorporation of active ingredients (sonoporation), as well as a process for the production of these particles and agents.

There have been microparticulate systems for controlled release of active ingredients for many years. A considerable number of possible shell substances and active ingredients can be used to this end. Also, there is a whole series of different production processes. Summaries on the shell substances and production processes used are found in, e.g.: M. Bornschein, P. Melegari, C. Bismarck, S. Keipert: Mikro- und Nanopartikeln als Arzneistoffträgersysteme unter besonderer Berücksichtigung der Herstellungsmethoden [Microparticles and Nanoparticles as Pharmaceutical Carrier Systems with Special Consideration of the Production Methods], Pharmazie [Pharmaceutics] 44 (1989) 585–593 and M. Chasin, R. Langer (eds.): Biodegradable Polymers as Drug Delivery Systems, Marcel Dekker, New York, 1990.

The release of active ingredients from microparticulate systems is based mainly on diffusion or erosion processes [cf. C. Washington: Drug Release from Microdisperse Systems: A Critical Review, Int. J. Pharm. 58 (1990) 1–12 and J. Heller: Bioerodible Systems, in: R. S. Langer, D. L. Wice (eds.): Medical Applications of Controlled Release Vol. 1, CRC Press, Florida, 1984, pp. 69–101].

These principles are, however, associated with the drawback that the time controllability of the release of active ingredients from microdisperse systems in vivo is limited to the speed of the erosion process and/or diffusion process and can no longer be influenced after administration.

The previously known concepts for local control of the release of active ingredients in vivo from microparticulate systems are based almost exclusively either on non-specific concentrations of the microparticulate active ingredient carrier in certain target organs such as the liver and spleen or on measures for ensuring specific alteration of the organ distribution in vivo after administration by the alteration of the surface properties of the microparticulate systems by means of surfactants or specificity-mediating substances such as, e.g., antibodies (cf.: R. H. Müller: Colloidal Carriers for Controlled Drug Delivery—Modification, Characterization and In Vivo Distribution—, Kiel, 1989; S. D. Tröbster, U. M üller, J. Kreuter: Modification of the Biodistribution of Poly(methylmethacrylate) Nanoparticles in Rats by Coating with Surfactants, Int. J. Pharm. 61 (1991), 85–100; S. S. Davis, L. Ilium, J. G. Mevie, E. Tomlinson (eds.); Microspheres and Drug Therapy, Elsevier Science Publishers B. V., 1984, and H. Tsuji, S. Osaka, H. Kiwada: Targeting of Liposomes Surface-Modified with Glycyrrhizin to the Liver, Chem. Pharm. Bull. 39 (1991) 1004–1008]. Other than this, however, all these processes offer no other means of actively influencing the site of the release of active ingredients after administration. In addition, it is not possible to influence the extent and the speed of the release of active ingredients after administration.

First attempts to actively influence the site of the release of active ingredients are based on the possibility of using existing or induced pH or temperature differences to induce release [cf: H. Hazemoto, M. Harada, N. Kamatsubara, M. Haga, Y. Kato: PH-Sensitive Liposomes Composed of Phosphatidyl-ethanolamine and Fatty Acid, Chem. Pharm. Bull. 38 (1990) 748–751 and J. N. Weinstein, R. L. Magin, M. B. Gatwin, D. S. Zaharko: Liposomes and Local Hyperthermia, Science 204 (1979) 188–1911. These methods are associated with the drawback, however, that they are either limited to cases where the necessary temperature or pH differences already exist (e.g., in tumor tissue) or the suitable parameters that are necessary for release must be created only by expensive, in some cases invasive, measures. Moreover, in the latter case, the local dissolution is small.

Another known process for influencing the site of the release of active ingredients involves the use of microparticles which can be concentrated by ferrofluids that are encapsulated in the particles over magnetic fields for external application within certain body segments [K. J. Widder, A. E. Senyei: Magnetic Microspheres: A Vehicle for Selective Targeting of Drugs, Pharmac. Ther. 20 (1983) 377–395). The use of such microparticles, however, requires the simultaneous specific use of powerful, easily focussed magnetic fields. Magnets that produce such fields are little used in medicine, however. In addition, the speed of the release of active ingredients cannot be influenced in this way.

In U.S. Pat. No. 4,657,543, a process in which release is brought about by the action of ultrasound on polymer blocks that contain active ingredients is described. This effect is based basically on an improved erosion of the polymer under the action of sound. The drawback to this process is that it is suitable only for stationary implants. For significant effects, moreover, the use of very high sonic pressures or of continuous acoustic signals is necessary, which can lead to tissue damage.

Liposomes that can be destroyed by irradiation with ultrasound that lies in the range of the resonance frequency of the microbubbles are described in WO 92/22298. In this process, the encapsulated active ingredient emerges. The resonance frequency is indicated as being about 7.5 MHz. Diagnostic ultrasound of such a high frequency exhibits only a small penetration depth (a few centimeters), however, due to the high absorption by body tissue. The liposomes described are therefore suitable for releasing active ingredients only in regions of the body that are near the surface.

When nucleic acids are used as active ingredients, two systems based on viral vectors or nonviral vectors are described in the literature. At this time, retro-, adeno and herpes viruses (or their recombinants) are being studied in vivo as viral vectors, and liposomes and ligands of cell surface-specific receptors are being researched in vivo as nonviral vectors (G. Y. Wu & C. H. Wu: Delivery Systems for Gene Therapy, Biotherapy, 3 (1991) 87–95 and F. D. Ledley: Are Contemporary Methods for Somatic Gene Therapy Suitable for Clinical Applications?, Clin Invest Med 16 (1) (1993) 78–88.

Initial studies on the use of gene therapy in humans concentrate on genetically caused diseases, such as, e.g., α-1-antitrypsin deficiency, cystic fibrosis, adenosinedeaminase deficiency and malignant tumors, such as, e.g., melanoma, breast neoplasms and intestinal carcinomas.

As yet, however, no vectors that make it possible to control the release of nucleic acids in both space and time are known.

Therefore, for a wide variety of purposes, there is still a need for formulations that can be administered specifically and that overcome the mentioned drawbacks of the prior art, i.e., in which both the site and time of the release of active ingredients and the amount of substance released can be controlled specifically by simple, noninvasive measures. The formulations, moreover, should exhibit high stability, especially with respect to mechanical influences.

The object of the invention is thus to make available such formulations, as well as to provide processes for their production.

This object is achieved by the invention:

It has been found that in the case of microparticulate systems that consist of a physiologically compatible suspension medium and microparticles that consist of a biodegradable shell and a core that contains gas and active ingredients, when irradiation is done with diagnostic ultrasound waves that lie in a frequency range which is below the resonance frequency of the particles, surprisingly enough, the shell of this particle is destroyed and the encapsulated active ingredient(s) is (are) thus specifically released.

The invention thus relates to new microparticles containing active ingredients, which contain a gas, a gaseous phase or gas mixtures in addition to the active ingredient, as well as microparticulate systems that consist of the microparticles according to the invention, as well as a pharmaceutically compatible suspension medium.

The particles exhibit a density that is less than 0.8 g/cm$^3$, preferably less than 0.6 g/cm$^3$, and have a size in the range of 0.1–8 μm, preferably 0.3–7 μm. In the case of encapsulated cells, the preferred particle size is 5–10 μm. Due to the small size, after i.v. injection they are dispersed throughout the entire vascular system. While being observed visually on the monitor of a diagnostic ultrasound device, a release of the contained substances that is controlled by the user can be brought about by stepping up the acoustic signal, whereby the frequency that is necessary for release lies below the resonance frequency of the microparticles. Suitable frequencies lie in the range of 1–6 MHz, preferably between 1.5 and 5 MHz.

As a result, combined control of the rate of release of active ingredients and the site of release of active ingredients by the user within the entire body is possible for the first time. This release, by destruction of the particle shell, can be achieved, surprisingly enough, with ultrasound frequencies that are far below the resonance frequency of the microbubbles with sonic pressures that are commonly encountered in medical diagnosis, without resulting in tissue heating. This is especially noteworthy because, due to the great mechanical stability of the particle shell—as is advantageous, e.g., with respect to the storage stability—destruction of the shell with relatively low-energy radiation would not be expected.

The release of active ingredients can be controlled owing to the high gas portion of the particle and the associated echogeneity, in vivo with the reduction of the received ultrasound signal.

Further, it has been found that when microparticulate systems according to the invention are used, improved transfer of active ingredients to the cells can be achieved (sonoporation).

Furthermore, it has been found that the active ingredients that are released from the microparticulate systems according to the invention show increased pharmacological effectiveness, surprisingly enough, compared to the pure active ingredient.

Owing to their properties, the microparticulate systems according to the invention are suitable for specific release of active ingredients and their increased transfer to the target cells under the action of diagnostic ultrasound.

As shell materials for the microparticles that contain gas/active ingredient, basically all biodegradable and physiologically compatible materials, such as, e.g., proteins such as albumin, gelatin, fibrinogen, collagen as well as their derivatives, such as, e.g., succinylated gelatin, crosslinked polypeptides, reaction products of proteins with polyethylene glycol (e.g., albumin conjugated with polyethylene glycol), starch or starch derivatives, chitin, chitosan, pectin, biodegradable synthetic polymers such as polylactic acid, copolymers consisting of lactic acid and glycolic acid, polycyanoacrylates, polyesters, polyamides, polycarbonates, polyphosphazenes, polyamino acids, poly-ξ-caprolactone as well as copolymers consisting of lactic acid and ξ-caprolactone and their mixtures, are suitable. Especially suitable are albumin, polylactic acid, copolymers consisting of lactic acid and glycolic acid, polycyanoacrylates, polyesters, polycarbonates, polyamino acids, poly-ξ-caprolactone as well as copolymers consisting of lactic acid, and ξ-caprolactone.

The enclosed gas(es) can be selected at will, but physiologically harmless gases such as air, nitrogen, oxygen, noble gases, halogenated hydrocarbons, $SF_6$ or mixtures thereof are preferred. Also suitable are ammonia, carbon dioxide as well as vaporous liquids, such as, e.g., steam or low-boiling liquids (boiling point <37° C.).

The pharmaceutical active ingredient can also be selected at will. As examples, pharmaceutical substances, toxins, viruses, virus components, components of bacteriological cell walls, peptides, such as, e.g., endothelin, proteins, glycoproteins, hormones, soluble messenger substances, dyes, complement components, adjuvants, trombolytic agents, tumor necrosis factors, cytokines (such as, e.g., interleucines, colony-stimulating factors such as GM-CSF, M-CSF, G-CSF) and/or prostaglandins, can be mentioned. The microparticles according to the invention are especially suitable for encapsulation of nucleic acids, whole cells and/or cell components, which are to be released (e.g., in the case of gene therapy) in the target organ by means of ultrasound.

The term pharmaceutical active ingredient includes both natural active ingredients and active ingredients that are produced synthetically or by genetic engineering.

Preferably, pharmaceutical active ingredients whose administered doses (in the case of bolus injection) do not exceed 100 mg per administration are used. In this case, it can be taken into consideration that in the microparticulate systems according to the invention, as described above, an increase in pharmacological effectiveness is achieved, whereby in various cases, an increased action can be observed, thus meaning that the microparticulate systems according to the invention can also be used for active ingredients, which in the conventional way must be administered in bolus doses of more than 100 mg per administration.

If still higher dosages are necessary, it is advisable to administer the agents over a prolonged period as infusion solutions.

Although there are no restrictions other than the above-mentioned limitations, the microparticulate systems according to the invention can be used especially advantageously in cases where, owing to a short in vivo service life of the active ingredient in free form, it is not possible or is possible only to a limited extent to reach the target organ without decomposition of the active ingredient occurring ahead of time. Such active ingredients include various hormones, peptides, proteins, cells and their components as well as nucleic acids.

A process for the production of the microparticles according to the invention consists of the fact that first gas-filled microparticles are produced in a way known in the art (DE 38 03 972, WO 93/00933, EP 0 514 790, WO 92/17213, U.S. Pat. No. 5,147,631, WO 91/12823, EP 0 048 745). According to the invention, the latter are then filled with active ingredients that are dissolved in supercritical gases. To this end, the gaseous microparticles that are dried with suitable processes (e.g., freeze-drying) are treated in an autoclave with a solution of the active ingredient in a supercritical gas. Suitably, the procedure is to introduce active ingredients and gas-filled microparticles together into an autoclave and then to fill the latter with the supercritical gas or gas mixture. As supercritical gases, all gases that can be converted to a supercritical state, but especially supercritical carbon dioxide, supercritical nitrogen, supercritical ammonia as well as supercritical noble gases, are suitable, depending on the active ingredient. After the microparticles are treated with the solution of the active ingredient in the supercritical gas or gas mixture, excess active ingredient on the outside surface of the microparticles is removed, if necessary, by washing the microparticles in a suitable medium, and the particles thus cleaned are optionally freeze-dried. This process is suitable for all active ingredients that are dissolved in supercritical gases or gas mixtures, such as, e.g., peptides or lipophilic pharmaceutical substances.

An alternative process, which is suitable especially for encapsulation of active ingredients that are insoluble in supercritical gases or gas mixtures (such as, e.g., proteins, sugar-containing compounds), is based on the encapsulation of an active ingredient-containing aqueous phase with the aid of a multiple emulsion. Water/oil/water (W/O/W) emulsions have proven especially suitable. To this end, the shell material is dissolved in a suitable organic solvent, which is not soluble in water, at a concentration of 0.01–20% (m/V). In this solution, an aqueous solution of the active ingredient to be encapsulated is emulsified, so that an emulsion of type W/O results. Both solutions can contain additional adjuvants, such as emulsifiers. It is preferred, however, because of the generally limited biological compatibility of emulsifiers, to largely dispense with the latter. It has proven advantageous to add pharmaceutically acceptable quasi-emulsifiers, such as, e.g., polyvinyl alcohol, polyvinylpyrrolidone, gelatin, albumin or dextrans in the concentration range of 0.1 to 25% to the inner aqueous phase. It has proven especially advantageous, in the inner aqueous phase, optionally in addition to the other adjuvants used, to dissolve 0.1–20% (m/V) of a readily water-soluble pharmaceutically acceptable salt or sugar or sugar alcohol, such as, e.g., sodium chloride, galactose, mannitol, lactose, saccharose, glucose, sodium hydrogen phosphate. It can be advantageous, moreover, to saturate the inner aqueous phase before emulsification with the organic phase used. The emulsion of type W/O produced should exhibit an average droplet size of the inner phase of about 0.1 to 10 $\mu$m. While being stirred, this emulsion is added to at least an equal volume of an aqueous solution of an emulsifier or quasi-emulsifier. While being stirred, the organic solvent is again removed by a suitable process (solvent evaporation). The water-filled microparticles obtained are washed, if necessary, and then dried, so that the inner water phase is removed without destroying the microparticles. In principle, suitable drying processes are freeze-drying and spray-drying. Freeze-drying is preferred. To this end, a building adjuvant such as, e.g., sugar, sugar alcohols, gelatin, gelatin derivatives, albumin, amino acids, polyvinylpyrrolidone, polyvinyl alcohol, is dissolved at a concentration of about 0.5–20% (m/V) in the suspension of microparticles. The suspension is then frozen at a lowest possible temperature, preferably below about −30° C., and then freeze-dried. After freeze-drying and redispersion in a suitable suspension medium, the gaseous microparticles of the necessary density that are produced can be separated by flotation or centrifuging from optionally also present solid or, increasingly, water-filled microparticles and, if necessary, as much as possible with the addition of building agents, again freeze-dried. The microparticles then contain the encapsulated active ingredient and gas or gaseous phase side by side.

The production of the microparticulate systems according to the invention from the particles that are produced according to the previously described processes is carried out by resuspending particles in a pharmaceutically compatible suspension medium. The resuspending in a suitable medium can be tied directly to the last process step (the freeze-drying), but can optionally also be carried out by the attending physician just before administration.

In the latter case, the microparticulate systems according to the invention are present as a kit that consists of a first container that contains the particles, and a second container that contains the suspension medium. The size of the first container is to be selected in such a way that the latter also has plenty of room for the suspension medium. Thus, e.g., with the aid of a syringe via a membrane located in the seal of the first container, the suspension medium can be added completely to the particles, and the suspension that is ready for injection can be produced by subsequent shaking. As suspension media, all injectable media that are known to one skilled in the art, such as, e.g., physiological common salt solution, water p.i. or 5% glucose solution, are suitable.

The amount administered depends on the active ingredient enclosed in each case. As a rough upper limit, a value can be assumed, as would also be used in conventional administration of the respective active ingredient. Because of the action-enhancing effect as well as the possibility of releasing the active ingredient specifically from the microparticulate system according to the invention, the necessary dose, however, generally lies below this upper limit.

The following examples are used to explain the object of the invention, without intending that they be limited to this object.

EXAMPLE 1

Caffeinic Microparticles That Consist of Polycyanoacrylate

Gas-filled microparticles that were produced from butyl cyanoacrylic acid according to DE 38 03 972 are freeze-dried with the addition of 2% (m/V) polyvinyl alcohol. About $3 \cdot 10^9$ particles in lyophilizate form are filled together with 50 mg of caffeine into an autoclave. The mixture is treated with carbon dioxide at about 45° C. and 100–120 bar. The removal of excess caffeine is done as follows: the microparticles that are removed in the autoclave are resuspended in 3 ml of water, which contains, dissolved, 1% Lutrol F 127. The particles are separated by centrifuging and resuspended in 3 ml of water, which contains, dissolved, 1% Lutrol F 127. The centrifuging with subsequent redispersion in 3 ml of water, which contains, dissolved, 1% Lutrol F 127, is repeated until no more caffeine can be detected photometrically at 273 nm in the water.

EXAMPLE 2

Fibrinolytic Microparticles That Consist of Poly (D, L-lactic acid-glycolic acid)

2 g of poly(D,L-lactic acid-glycolic acid) (50:50) (Resomer RG 503, Boehringer Ingelheim) is dissolved in 20 ml of $CH_2Cl_2$. 10 mg of r t-PA (tissue plasminogen activator) is dissolved in 4 ml of a 4% aqueous gelatin solution, which was previously autoclaved, and added to the organic phase while being stirred with a fast stirrer. After emulsification is completed, 200 ml of a 4% autoclaved gelatin solution is added with additional stirring. The emulsion is stirred for 8 hours at room temperature. The particles that are produced are filtered with a 5 μm filter, separated by centrifuging, resuspended in 50 ml of 4% autoclaved gelatin solution, frozen at $-78°$ C. and freeze-dried. After resuspension, the gaseous microparticles are separated by centrifuging (at 1000 rpm, 30 minutes). The gaseous microparticles are taken up in 20 ml of water for injection purposes. They have a density of less than 0.7 $g/cm^3$.

EXAMPLE 3

In Vitro Release of Caffeine by Ultrasound 1 ml of a particle suspension that is prepared according to Example 1, diluted with water to a concentration of $10^8$ particles/ml, is added to a beaker filled with 100 ml of degassed water. A 3.5 MHz transducer of a diagnostic ultrasound device (HP Sonos 1000) is immersed in the water, and the change in the B-image is observed. First, the device is operated at an average sonic output (Transmit≦20 dB), in which case clear echoes can be detected. A test of the particle-free water on caffeine is negative. If the sonic pressure is increased (Transmit>30 dB), the echoes disappear. The liquid now contains detectable free caffeine, mainly fragments of microparticles, and only a very few intact microparticles can be detected by microscope.

EXAMPLE 4

In Vivo Release of Recombinant Tissue Plasminogen Activator (r t-PA) by Ultrasound 1 ml of a particle suspension that is prepared according to Example 2, diluted with water to a concentration of $10^8$ particles/ml, is added to a beaker filled with 100 ml of degassed water. A 3.5 MHz transducer of a diagnostic ultrasound device (HP Sonos 1000) is immersed in the water, and the change in the B-image is observed. First, the device is operated at a low sonic output (Transmit~10 dB), in which case clear echoes can be detected. A test of the particle-free water on r t-PA is negative. If the sonic pressure is increased (Transmit>30 dB), the echoes disappear. The liquid now contains detectable free r t-PA, mainly fragments of microparticles and only a very few intact microparticles can be detected by microscope. The particle suspension that is treated at increased sonic pressure exhibits fibrinolytic properties.

EXAMPLE 5

Mitomycin-Containing Microparticles that Consist of Polylactic Acid 2 g of polylactic acid (MG about 20,000) is dissolved in 100 ml of $CH_2Cl_2$. 20 mg of mitomycin is dissolved in 15 ml of 0.9% aqueous common salt solution and added to the organic phase while being stirred with a fast stirrer. After emulsification is completed, 200 ml of a 1% solution of polyvinyl alcohol (MG about 15,000) in water is added with additional stirring. The emulsion is stirred for 4 hours at room temperature. The particles that are produced are filtered with a 5 μm filter, separated by centrifuging, resuspended in 50 ml of a 5% solution of polyvinylpyrrolidone (MG about 10,000) in water, frozen at $-50°$ C. and then freeze-dried. After resuspension, the gaseous microparticles are separated by centrifuging (at 1000 rpm, 30 minutes). The gaseous microparticles are taken up in 20 ml of water for injection purposes. They have a density of less than 0.7 $g/cm^3$. They are suitable also as contrast media for ultrasound and release mitomycin in the case of acoustic irradiation with diagnostic ultrasound.

EXAMPLE 6

Vincristine Sulfate-Containing Microparticles that Consist of Poly-ξ-caprolactone 2 g of poly-ξ-caprolactone (MG about 40,000) is dissolved in 50 ml of $CH_2Cl_2$. 10 mg of vincristine sulfate is dissolved in 15 ml of a 5% aqueous solution of galactose and added to the organic phase while being stirred with a fast stirrer. After emulsification is completed, 200 ml of a 5% solution of human serum albumin in water is added with further stirring. The emulsion is stirred for 4 hours at room temperature. The particles that are produced are filtered with a 5 μm filter, separated by centrifuging, resuspended in 50 ml of a 5% solution of human serum albumin in water, frozen at $-50°$ C and then freeze-dried. After resuspension, the gaseous microparticles are separated by centrifuging (at 1000 rpm, 30 minutes). The gaseous microparticles have a density of less than 0.7 $g/cm^3$. They are suitable as contrast media for ultrasound and release vincristine sulfate in the case of acoustic irradiation with diagnostic ultrasound.

EXAMPLE 7

Ilomedin-Containing Microparticles that Consist of Polycyanoacrylic Acid Butyl Ester 3 g of polycyanoacrylic acid butyl ester is dissolved in 50 ml of $CH_2Cl_2$. 1 mg of ilomedin is dissolved in 15 ml of a 5% aqueous solution of galactose and added to the organic phase while being stirred with a fast stirrer. After emulsification is completed, 200 ml of a 5% solution of polyvinyl alcohol (MG 15,000) in water is added with additional stirring. The emulsion is stirred for 4 hours at room temperature. The particles that are produced are filtered with a 5 μm filter, separated by centrifuging, resuspended in 50 ml of a 10% solution of lactose in water, frozen at $-50°$ C. and then freeze-dried. After resuspension, the gaseous microparticles are separated by centrifuging (at 1000 rpm, 30 minutes). The gaseous microparticles have a density of less than 0.7 $g/cm^3$. They are suitable as contrast media for ultrasound and release ilomedin in the case of acoustic irradiation with diagnostic ultrasound.

EXAMPLE 8

Methylene Blue-Containing Microparticles that Consist of Poly(D,L-Lactic Acid-Glycolic Acid)

4 g of poly (D,L-lactic acid-glycolic acid) (50:50) (Resomer RG 503, Boehringer Ingelheim) is dissolved in 50 ml of $CH_2Cl_2$. 20 mg of methylene blue is dissolved in 4 ml of a 4% aqueous gelatin solution, which was previously autoclaved, and added to the organic phase while being stirred with a fast stirrer. After emulsification is completed, 200 ml of a 4% autoclaved gelatin solution is added with additional stirring. The emulsion is stirred for 8 hours at room temperature. The particles that are produced are filtered with a 5 μm filter, separated by centrifuging, resuspended in 50 ml of 4% autoclaved gelatin solution, frozen at −78° C. and freeze-dried. After resuspension, the gaseous microparticles are separated by centrifuging (at 1000 rpm, 30 minutes). The gaseous microparticles are taken up in 20 ml of water for injection purposes. They have a density of less than 0.7 g/cm$^3$ and release methylene blue in the case of acoustic irradiation with ultrasound (sonic pressure>50 dB, frequency 2.5 MHz).

EXAMPLE 9

Nucleic Acid-Containing Microparticles (Marker Gene β-Gal+Albumin Promoter) that Consists of Poly(D,L-Lactic Acid-Glycolic Acid)

0.4 g of polyvinylpyrrolidone (k<18) and 2 g of a copolymer that consists of lactic acid and glycolic acid 50:50 are dissolved in 50 ml of $CH_2Cl_2$. While being stirred, 5 ml of a solution of 300 μg of marker gene β-Gal with albumin promoter is added to 0.9% common salt solution. The emulsion that is produced is transferred into 200 ml of a 2% autoclaved (121° C., 20 minutes) gelatin solution while being stirred. After 3 hours, the suspension that is produced is decanted in portions of 5 ml each, frozen at −55° C. and then freeze-dried for 70 hours. After freeze-drying, the vials are resuspended with 5 ml of water each and allowed to stand for 3 hours. The floated particles are removed in 2 ml of water each, which contains 10% PVP, resuspended and after freezing at −55° C., again freeze-dried for 90 hours.

EXAMPLE 10

In Vitro Release of Nucleic Acid (Marker Gene β-Gal+Albumin Promoter) that Consists of Microparticles 1 vial of a nucleic-acid containing microparticle preparation, produced according to Example 9, is resuspended with 2 ml of water. 1 ml of the suspension is treated with ultrasound (sample 1), and 1 ml is not treated with ultrasound (sample 2). Both samples are centrifuged, and the particle-free phases are removed and filtered with a 0.2 μm filter. The filtrates are examined with the aid of gel electrophoresis to determine their contents of marker gene β-Gal. The filtrate that consists of sample 1 contains about 100% more β-Gal than the filtrate of sample 2.

EXAMPLE 11

In Vivo Release of Nucleic Acid (Marker Gene β-Gal+Albumin Promoter) that Consists of Microparticles Two vials of a nucleic acid-containing microparticle preparation, produced according to Example 9, are resuspended with 2 ml of water each. The entire resuspendate is administered slowly i.v. (about 0.5 ml/min) to the anesthetized rat. During administration, acoustic irradiation (7.5 MHz) of the liver is carried out, which is continued for up to 20 minutes after the end of the injection. 48 hours after particle administration, the liver is removed and quick-frozen in isopentane at −40° C. Enzyme-histochemical detection of neutral β-galactosidase is carried out on 8–10 μm thick frozen sections. Contrast staining is carried out with nuclear fast red. In the frozen section of the liver, the neutral β-galactosidase—as a result of the gene expression—was demonstrated diffusely dispersed as dark-blue signals.

We claim:

1. A microparticle solution comprising microparticles having a biodegradeable polymer shell and, incorporated within the shell, at least one pharmaceutically active ingredient releasable in vivo by application of ultrasound waves and a gaseous phase and having no pharmaceutically active ingredient in the solution other than within the microparticles, wherein the microparticle solution are prepared by treating in an autoclave microparticles comprising the biocompatible shell and gaseous phase with a solution of the at least one active ingredient in a supercritical gas.

2. The microparticle solution of claim 1, wherein the supercritical gas is supercritical carbon dioxide, supercritical nitrogen, supercritical ammonia or a supercritical noble gas.

3. The microparticle solution of claim 1, wherein the density of the microparticle solution is less than 0.8 g/$cm^3$.

4. The microparticle solution of claim 1, wherein the particle size of the microparticle solution is 0. 1–10 μm.

5. The microparticle solution of claim 1, wherein the biodegradeable polymer shell is comprised of proteins, gelatin, fibrinogen, collagen, crosslinked polypeptides, reaction products of proteins with polyethylene glycol, starch, chitin, chitosan, pectin, polylactic acid, copolymers consisting of lactic acid and glycolic acid, polycyanoacrylates, polyesters, polyamides, polycarbonates, polyphosphazenes, polyamnino acids, poly-ξ-caprolactone, copolymers consisting of lactic acid and ξ-caprolactone or combinations thereof.

6. The microparticle solution of claim 1, wherein the at least one pharmaceutically active ingredient is a toxin, virus, virus component, component of bacteriological cell walls, soluble messenger substance, dye, thrombolytic agent, tumor necrosis factor, nucleic acid, peptide, protein, glycoprotein, hormone, cytokine prostaglandin or combination thereof.

7. The microparticle solution of claim 1, wherein the at least one pharmaceutically active ingredient is cells and/or cell components.

8. The microparticle solution of claim 1, wherein the gaseous phase comprises air, nitrogen, oxygen, carbon dioxide, noble gases, ammonia, halogenated or partially halogenated hydrocarbon, $SF_6$, steam, a liquid with a boiling point <37° C. or combinations thereof.

9. The microparticle solution of claim 1, wherein the pharmaceutically active ingredient is at least one nucleic acid, peptide, protein, glycoprotein, hormone or prostaglandin.

10. A method for in-vivo release of an active ingredient which comprises:

providing in-vivo a microparticle solution having microparticles comprising a shell of a biodegradable polymer which is a gelatin, fibrinogen collagen crosslinked polypeptide reaction producer of proteins with polyethylene glycol, starch, chitin, chitosan, pectin, polylactic acid, copolymer consisting of lactic acid and glycolic acid, polycyanoacrylate, polyester, polyamide, polycarbonate, polyphosphazene polyamino acid, poly-ξ-caprolactone, copolymer consisting of lactic acid and ξ-caprolactone or a mixture thereof; and incorporated therein a gaseous phase and at least one pharmaceutically active ingredient, the solution having no pharmaceutically active ingredient other than within the microparticles, and applying ultrasound waves to the microparticles such that the shell is destroyed and the at least one pharmaceutically active ingredient is released in-vivo only at this time.

11. The method according to claim 10, wherein the density of the microparticle solution is less than 0.8 g/$cm^3$.

12. The method according to claim 10, wherein the particle size of the microparticle solution is from 0.1–10 μm.

13. The method according to claim 10, wherein the biodegradable polymer is a protein, gelatin, fibrinogen, collagen, crosslinked polypeptide, reaction product of proteins with polyethylene glycol, starch, chitin, chitosan, pectin, polylactic acid, copolymer consisting of lactic acid and glycolic acid, polycyanoacrylate, polyester, polyamide, polycarbonate, polyphosphazene, polyamino acid, poly-ξ-caprolactone, copolymer consisting of lactic acid and ξ-caprolactone or a mixture thereof.

14. The method according to claim 10, wherein the at least one active ingredient is a toxin, virus, virus component, component of bacteriological cell walls, soluble messenger substance, dye, thrombolytic agent, tumor necrosis factor, nucleic acid, peptide, protein, glycoprotein, hormone, cytokine, prostaglandin or combination thereof.

15. The method according to claim 10, wherein the at least one active ingredient is cells and/or their components.

16. The method according to claim 10, wherein the gaseous phase is air, nitrogen, oxygen, carbon dioxide, a noble gas, ammonia, a halogenated or partially halogenated hydrocarbon, $SF_6$, steam, a liquid having a boiling point <37° C. or mixtures thereof.

17. The method of claim 10, wherein the ultrasound waves are applied at a frequency of 1–6 MHZ.

18. The method of claim 10, wherein the ultrasound waves are applied at a frequency of 1.5–5 MHZ.

19. The method of claim 10, wherein the ultrasound waves are applied at a frequency below the resonance frequency of the microparticles.

20. Process for the production of microparticle solution containing a gaseous phase and at least one pharmaceutically active ingredient releasable in vivo by application of ultrasound waves which comprises treating in an autoclave microparticle solution comprising a gaseous phase in a biocompatible shell with a solution of the at least one pharmaceutically active ingredient in a supercritical gas.

21. The process of claim 19, wherein the supercritical gas is supercritical carbon dioxide, supercritical nitrogen, supercritical ammonia supercritical noble gas, or a combination thereof.

22. The process of claim 20, wherein the treated microparticle solution are subsequently washed to remove active ingredient not incorporated within the biocompatible shell.

23. The process of claim 20, wherein the treated microparticle solution are subsequently freeze-dried.

* * * * *